United States Patent [19]

Hughes et al.

[11] Patent Number: 5,500,140
[45] Date of Patent: Mar. 19, 1996

[54] OIL-SOLUBLE PHOSPHORUS- AND NITROGEN-CONTAINING ADDITIVES

[75] Inventors: Joe Hughes, Ballwin, Mo.; Rolfe J. Hartley, Glen Allen; Vasudevan Balasubramaniam, Richmond, both of Va.

[73] Assignee: Ethyl Corporation, Richmond, Va.

[21] Appl. No.: 422,407

[22] Filed: Mar. 31, 1995

[51] Int. Cl.⁶ .................................................. C10M 125/20
[52] U.S. Cl. .......................... 252/46.7; 252/46.6; 558/158
[58] Field of Search ........................... 558/158; 252/46.6, 252/46.7

[56] References Cited

U.S. PATENT DOCUMENTS

| | | | |
|---|---|---|---|
| 3,197,405 | 7/1965 | LeSuer | 252/32.7 |
| 3,197,496 | 7/1965 | LeSuer | 260/461 |
| 4,155,958 | 5/1979 | Fields | 260/926 |
| 4,435,338 | 3/1984 | Michaelis et al. | 260/929 |

OTHER PUBLICATIONS

CA91:90647x Beta–phosphosulfoxy alcohols. Fields, p. 696, 1979.

*Primary Examiner*—Joseph K. McKane
*Attorney, Agent, or Firm*—Dennis H. Rainear; William H. Thrower

[57] ABSTRACT

Additives are produced by (i) reacting an O,O-dihydrocarbyl phosphorodithioic acid with a monoepoxide or mixture of monoepoxides having in the range of 20 to about 30 carbon atoms in the molecule, (ii) reacting the product with phosphorus pentoxide to produce an acid phosphate intermediate, and (iii) neutralizing the intermediate with at least one amine. At least 50 mole %, and preferably all, of the hydrocarbyl groups of the O,O-dihydrocarbyl phosphorodithioic acid are secondary acyclic hydrocarbyl groups free of acetylenic unsaturation. The balance, if any, of such hydrocarbyl groups are primary acyclic hydrocarbyl groups free of acetylenic unsaturation. The additives are multifunctional in that they have limited slip properties, antiwear/extreme pressure properties, and corrosion inhibiting properties.

35 Claims, No Drawings

OIL-SOLUBLE PHOSPHORUS- AND NITROGEN-CONTAINING ADDITIVES

TECHNICAL FIELD

This invention relates to novel metal-free phosphorus- and nitrogen-containing compositions that are useful as multifunctional additives in oils of lubricating viscosity.

BACKGROUND

Although a substantial number of gear oils are available in the marketplace, there exists a need for further improvements in limited slip or enhanced positraction performance.

It is known that the high pressures occurring in certain gears and bearings may cause a lubricant film to rupture so that opposing metal surfaces contact each other. This metal contact results in scuffing, seizure, excessive wear, loss of efficiency, and ultimately in the failure of the mechanism. In addition, these high pressures on the oil film effect a rise in internal heat which may be increased by any friction resulting from the metal contacts through breaks in the oil film. Consequently, mechanisms in which high mechanical pressures are likely to occur between interacting metal surfaces require lubricants that have both high lubricity and high film strength or extreme pressure properties.

Unfortunately, these two requirements are frequently antipathetic to each other. That is, an additive which has high film strength does not necessarily have good lubricity or "oiliness" and may in fact increase friction and heating in the oil film. Conversely, an additive having good lubricity or "oiliness" does not necessarily have good extreme pressure properties, and may in fact mask or interfere with the action of a separate extreme pressure additive component.

Limited slip axles or differentials are mechanisms which transmit the greater driving force to the vehicular wheel that has the better traction. Such mechanisms have a special lubrication problem peculiar unto themselves. The interplay of pressures and forces during turns under load often results in noise, often referred to as "chatter", and vibration or shudder of the vehicle. In order to function properly, limited slip axles or differentials require, among other things, lubricants that have both high lubricity and high film strength or extreme pressure properties, requirements which, as noted above, are frequently antipathetic to each other.

Prior attempts to overcome this "chatter" problem generally involved research on and utilization of friction-reducing agents or oiliness agents which were added to the base lubricant. In that approach it was necessary to avoid upsetting the balance between extreme pressure, antiwear, and rust and corrosion protection as well as the oxidative stability afforded by the additive complements utilized in such lubricants. A very desirable advance in the art would be the provision of additive compositions that have the capability of providing both limited slip properties and antiwear/extreme pressure properties to a lubricating oil composition in which they are employed. Such an additive would enable the formulation of lubricants which avoid or at least minimize the "chatter" problem, contribute antiwear/extreme pressure properties, and at the same time make it possible to avoid the complications brought about by use of conventional friction-reducing additives in the lubricant. An additive possessing such multifunctionality is rarely, if ever, encountered in the art.

U.S. Pat. Nos. 3,197,405 and 3,197,496 contain extensive descriptions of phosphorus- and nitrogen-containing products formed by reaction of a hydroxy-substituted triester of a phosphorothioic acid with particular inorganic phosphorus reagents, and neutralization of the product with an amine. These products are indicated to be useful as insecticides, corrosion inhibitors, rust inhibitors, antiwear agents, and are indicated to be especially effective as corrosion inhibiting and extreme pressure additives in lubricating compositions. According to these patents, the hydroxy-substituted phosphorothioate triester may be formed in various ways including reaction of an O,O-dihydrocarbyl phosphorodithioic acid with an epoxide or glycol. The preferred epoxides are aliphatic epoxides having less than about 8 carbon atoms and styrene oxides. Other acyclic aliphatic epoxides mentioned are 1,2-octene oxide, dodecene oxide and octadecene oxide.

U.S. Pat. No. 4,435,338 describes products made by reaction of an O,O -dialkyl dithiophosphate with a difunctional, trifunctional or tetrafunctional epoxide compound.

THE INVENTION

Novel and eminently useful multifunctional additives having, inter alia, limited slip properties are provided by this invention. More particularly products having limited slip properties as well as antiwear/extreme pressure and corrosion inhibiting properties are produced by forming a hydroxy-substituted phosphorothioate by (i) reacting an O,O-dihydrocarbyl phosphorodithioic acid with a monoepoxide or mixture of monoepoxides having in the range of 20 to about 30 carbon atoms in the molecule, (ii) reacting this product with phosphorus pentoxide to produce an acid phosphate intermediate, and (iii) neutralizing at least a major proportion of the intermediate with at least one amine. At least 50 mole % of the hydrocarbyl groups of the O,O-dihydrocarbyl phosphorodithioic acid are secondary acyclic hydrocarbyl groups free of acetylenic unsaturation and the balance, if any, of such hydrocarbyl groups are primary acyclic hydrocarbyl groups free of acetylenic unsaturation. Preferably, essentially all of the hydrocarbyl groups (e.g., at least 98% of them) are secondary acyclic hydrocarbyl groups free of acetylenic unsaturation. In short, the lower the content of the primary hydrocarbyl groups, the better. Thus within reasonable limits of commercial practicality, O,O-dihydrocarbyl phosphorodithioic acids formed from substantially pure secondary alcohols should be used in the above first stage reaction.

Preferred products of this invention when formed from a 1,2-epoxide are composed principally of an oil-soluble phosphorus- and nitrogen-containing composition of the formula:

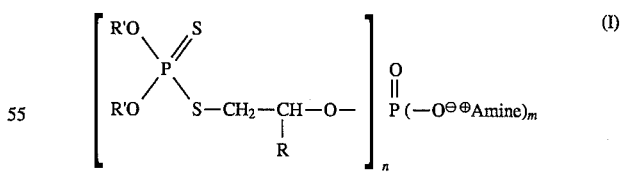

wherein R is at least one alkyl group, and preferably a mixture of alkyl groups having from 18 to about 28 carbon atoms, and preferably a mixture of alkyl groups having from 18 to about 22 carbon atoms; each R' is, independently, a secondary acyclic hydrocarbyl group free of acetylenic unsaturation and having 3 to 18 carbon atoms; Amine is, independently, a protonated primary or secondary amine; n is 1–2; m is 1–3; and the sum of n and m is no greater than 3. Typically, the product will further comprise a minor proportion (i.e., less than 50 mole %) of an isomeric form of the composition of Formula (I) above, namely an isomeric form having the formula:

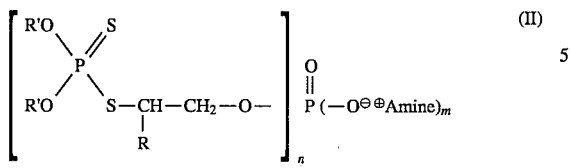

wherein R, R', Amine, n and m are as defined above

These preferred compositions of this invention can be prepared by (i) reacting a dihydrocarbyl phosphorodithioic acid of the formula:

wherein each R' is as defined above, with at least one 1,2-alkylene oxide having from 20 to about 30 carbon atoms in the molecule to form a dihydrocarbyl mono-(hydroxyalkyl) phosphorodithioate, (ii) reacting this triester with phosphorus pentoxide to form a substituted acid phosphate of the formula:

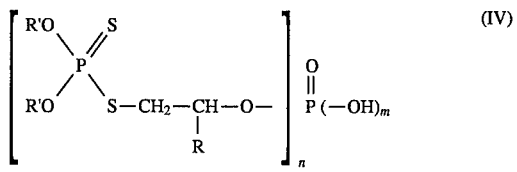

wherein R, R', Amine, n and m are as defined above, and (iii) neutralizing at least a substantial portion of this substituted acid phosphate with at least one primary or secondary amine. Typically, the acid phosphate (IV) will be accompanied by a minor proportion of an isomeric form of the acid phosphate, viz., an isomeric form having the formula:

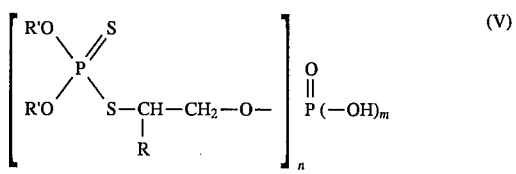

wherein R R', Amine, n and m are as defined above.

Preparation of the dihydrocarbyl phosphorodithioic acid is usually accomplished by reacting phosphorus pentasulfide with the appropriate alcohol, namely a secondary acyclic monohydric alcohol free of acetylenic unsaturation and having 3 to 18 carbon atoms in the molecule. Examples of such alcohols include 2-propanol, 2-butanol, 2-pentanol, 3-pentanol, and the higher secondary alkanol homologs up to and including the octadecanols, and the analogous secondary olefinically unsaturated alcohols such as 3-butenol-2, 3 -pentenol-2, 4-pentenol-2, and analogous secondary alkenols having up to about 18 carbon atoms per molecule. The olefinically unsaturated alcohols may contain from 1 to 3 olefinic double bonds. Mixtures of two or more alkanols can be employed. Likewise, mixtures of olefinically unsaturated alcohols can be used, as well as mixtures of at least one secondary alkanol and at least one secondary olefinically unsaturated alcohol. The reaction involves 4 moles of the alcohol per mole of the phosphorus pentasulfide. Reaction temperatures are normally in the range of about 50° to about 150° C. When mixtures of alcohols are used, as long as the mixture contains at least 50 mole % of secondary alcohol(s), there can be up to 50 mole % of primary alcohol(s) in the mixture. Preferably such mixtures contain no more than about 30 mole % primary and at least about 70 mole % secondary alcohol, and more preferably the mixture contains no more than about 10 mole % primary and at least about 90 mole % secondary alcohol. Use of one or a mixture of substantially pure secondary alcohols is preferred.

The most preferred type of secondary alcohols are branched-chain secondary alcohols, such as 4-methyl-2-pentanol, 4-methyl-2-hexanol, 5-methyl-2-hexanol, 6-methyl-3-heptanol, 5,7-dimethyl-3-octanol, and analogous secondary alkenols. Branched-chain secondary alcohols having from about 6 to about 12 carbon atoms are particularly preferred. Methyl branching is very desirable. Of the branched alcohols, 4-methyl-2-pentanol is presently the most preferred of all.

The reaction of the dihydrocarbyl phosphorodithioic acid with the monoepoxide to form the dihydrocarbyl mono-(hydroxyalkyl) phosphorodithioate is an exothermic reaction an thus is ordinarily initiated at, or somewhat below, room temperature and preferably is controlled so as not to exceed about 70° C. Most preferably the reaction is conducted at temperatures in the range of about 25° to about 50° C. It is also preferred to add the monoepoxide (an alkylene oxide, preferably a 1,2-alkylene oxide) in small portions to the dihydrocarbyl phosphorodithioic acid while continuously agitating the reaction mixture. After completing the reaction, the reaction mixture is typically maintained at about 50° C. with mild agitation for about one hour.

Formation of the substituted acid phosphate in the ensuing reaction between the dihydrocarbyl hydroxyalkyl triester and the phosphorus pentoxide also involves an exothermic reaction. Thus once again the reaction may be initiated at about room temperature and preferably is conducted at a temperature within the range of about 20° to about 60° C. Typically, the reactants are employed in proportions of about 2 to about 4 moles of the triester, and preferably about 3 moles, per mole of the $P_2O_5$. Preferably, the $P_2O_5$ is added portion-wise to the triester while agitating the reactants to ensure intimate contact between them. Upon completion of the reaction, it is desirable to maintain the reaction mixture at about 50° to 60° C. for about one hour while mildly agitating the mixture.

Neutralization of the substituted acid phosphate is readily accomplished simply by mixing the acid phosphate with one or more selected primary or secondary monoamines. Typically, this reaction is conducted at a temperature of about 20° and about 60° C. Once again, it is desirable to continue agitating the reaction mixture while holding the temperature in the range of about 50° to about 60° C. for a period of one hour.

Among suitable amines for use in the neutralization step are (a) monoalkyl amines in which the alkyl group is a primary alkyl group of 1 to about 30 carbon atoms such as methyl amine, ethyl amine, 1-propyl amine, 1-butyl amine, 2-methyl-1-propyl amine, 1-pentyl amine, 2-methyl-1-butyl amine, 3-methyl-1-butyl amine, 2,2 -dimethyl-1-propyl amine, 1-hexyl amine, 2-methyl-1-pentyl amine, 3 -methyl-1-pentyl amine, 4-methyl-1-pentyl amine, 2,2-dimethyl-1-butyl amine, 2,3-dimethyl-1-butyl amine, 3,3-dimethyl-1-butyl amine, 2-ethyl-1-butyl amine, and similar higher straight chain and branched chain monoalkyl amine homologs in which the primary alkyl group contains from 7 to about 30 carbon atoms; (b) monoalkyl amines in which the alkyl group is a secondary alkyl group of 3 to about 30 carbon atoms such as 2-propyl amine, 2-butyl amine, 2-pentyl amine, 3-pentyl amine, 3-methyl-2-butyl amine, 2-hexyl amine, 3-hexyl amine, 3-methyl-2-pentyl amine, 4-methyl- 2-pentyl amine, 2-methyl-3-pentyl amine, 3,3-dimethyl-2-butyl amine, and similar higher monoalkyl amine homologs in which the secondary alkyl group contains from 7 to about 30 carbon atoms; (c) monoalkyl amines in which the alkyl group is a tertiary alkyl group of 4 to about 30 carbon atoms such as 2-methyl-2-propyl amine, 2-methyl-2-butyl amine, 2-methyl-2-pentyl amine, 3-methyl-3-pentyl amine, 2,3-dimethyl-2-butyl amine, and similar higher monoalkyl amine homologs in which the tertiary alkyl group contains from 7 to about 30 carbon atoms; (d) ethylenically unsaturated acyclic monohydrocarbyl primary, secondary and tertiary amines such as allyl amine, the butenyl amines, the pentenyl amines, the hexenyl amines, the heptenyl amines, the octenyl amines, and similar higher homologs and analogs in which the alkenyl group contains from 9 to about 30 carbon atoms and from 1 to 3 ethylenic double bonds; (e) dialkyl amines in which the alkyl groups are primary, secondary and/or tertiary alkyl groups such as dimethyl amine, methyl ethyl amine, diethyl amine, dipropyl amine, dibutyl amine, diisobutyl amine, di-tert-butyl amine, dipentyl amine, dihexyl amine, diheptyl amine, dioctyl amine, and analogous compounds having straight and/or branched chain alkyl groups each having up to about 30 carbon atoms; (f) ethylenically unsaturated acyclic dihydrocarbyl primary, secondary and tertiary amines such as diallyl amine, butyl octenyl amine, ethyl oleyl amine, dioleyl amine, and analogous compounds having two ethylenically unsaturated groups each containing up to about 30 carbon atoms and from 1 to 3 ethylenic double bonds or one such ethylenically unsaturated group and one primary, secondary or tertiary alkyl group having up to about 30 carbon atoms. Mixtures of these various amines can be used. Commercially available amines such as stearyl amine, oleyl amine, mixtures of tertiary alkyl primary amines such as Primene 81R amine and Primene JM-T amine (Rohm & Haas Company) are preferred.

The compositions of this invention and their synthesis are illustrated by the following examples which are not intended to limit this invention in its generic aspects.

EXAMPLE 1

O,O-bis(4-methyl-2-pentyl) phosphorodithioic acid (59.7 g; 0.2 mole) is placed in a 300 Ml reaction flask equipped with a stirrer. With continuous stirring, 0.2 mole of a commercially available mixture of 1,2-alkylene oxides having 20 to 24 carbon atoms per molecule (VIKOLOX 20–24) is added dropwise and when the temperature has reached 45° C., the mixture is cooled so as to maintain the temperature between 45° and 50° C. When the addition is complete, the reaction mixture is stirred for one hour.

In the second stage reaction, phosphorus pentoxide (9.4 g; 0.066 mole) is added in 6 equal portions at intervals of approximately 10 minutes each. During the addition, the reaction mixture is continuously stirred and cooled to maintain the mixture at 50° to 55° C. Upon completion of the addition, the reaction mixture is held at this temperature range for one hour with stirring.

Neutralization, the third stage reaction, is effected by adding oleyl amine (Armeen OL) (55.6 g; 0.2 mole) dropwise to the product of the second stage reaction while holding the temperature at 50° to 55° C. The reaction mixture is stirred for one hour at 50°0 to 55° C. upon completion of the amine. The resultant product is a composition of this invention.

EXAMPLE 2

The procedure of Example 1 is repeated with the exception that 0.2 mole of a $C_{12-15}$ tertiary alkyl primary amine mixture (Primene 81 R) is used in place of the oleyl amine. The resultant product is a composition of this invention.

EXAMPLE 3

A composition of this invention is formed by repeating the procedure of Example 1 with the exception that the amine used is an equimolar mixture of 1-octadecyl amine and 2-octadecyl amine.

EXAMPLE 4

Upon repetition of Example 1, but using octyl amine (0.2 mole) instead of the oleyl amine, yields another composition of this invention.

EXAMPLE 5

Examples 1–4 are each repeated substituting 0.2 mole of O,O-bis(2-hexyl) phosphorodithioic acid for the O,O-bis(4-methyl-2-pentyl) phosphorodithioic acid. The resultant final products constitute compositions of this invention.

EXAMPLE 6

Examples 1–4 are each repeated substituting 0.2 mole of O,O-bis(5-methyl-3-hexyl) phosphorodithioic acid for the O,O-bis(4-methyl-2-pentyl) phosphorodithioic acid. The resultant final products constitute compositions of this invention.

EXAMPLE 7

The procedure of Example 1 is repeated except that 75.7 g (0.2 mole) of a commercially available mixture of 1,2-alkylene oxides having 24 to 28 carbon atoms per molecule (VIKOLOX 24–28) is used as the epoxide in the first stage reaction. The resultant final products are compositions of this invention. A product formed in this manner was found to contain 5.14% phosphorus and 6.38% sulfur, and to have an average molecular weight of about 1365.

EXAMPLE 8

The procedure of Example 7 is repeated except that the O,O-dihydrocarbyl phosphorodithioic acid used in the first stage is a mixed di-secondary alkyl phosphorodithioic acid formed from an equimolar mixture of 4-methyl-2-pentanol and 2-propanol. Thus the charge in the first stage reaction is 57.7 g (0.2 mole) of this mixed di-secondary alkyl phosphorodithioic acid and 75.7 g of the VIKOLOX 24-28 epoxide. A product formed in this manner was found to contain 5.19% phosphorus and 6.45% sulfur, and to have an average molecular weight of about 1350.

The excellent limited slip characteristics of the compositions of this invention have been demonstrated both by bench tests and by use of the "Big Wheel-Little Wheel" test procedure of General Motors Corporation as performed by Southwest Research Institute. In particular, a lubricant formulation containing 1.91 percent by weight of a product formed as in Example 1 was run in the LVFA limited slip bench test at room temperature. For purposes of comparison, (1) Oil A, a lubricant containing a recommended dosage level of a commercially available automotive gear oil package, (2) Oil B, the Oil A lubricant composition to which had been added a recommended dosage level of a commercially available limited slip top treat additive, and (3) Oil C, a passing General Motors limited slip reference oil formulation were subjected to the same test bench test procedure under the same test conditions. The results of these tests are summarized in Table 1, wherein the average percentage improvement is the improvement as compared to the performance in the same test of a failing reference oil used by General Motors Corporation as a test standard for failure.

TABLE 1

| Composition | Average Improvement, % | Standard Deviation |
| --- | --- | --- |
| Oil A | 3.618 | 2.625 |
| Oil B | 3.662 | 2.813 |
| Oil C | 7.547 | 3.703 |
| The Invention | 16.33 | 1.414 |

It will be seen that the results in Table 1 are statistically significant results.

Comparative tests were conducted in a vehicle using the Limited Slip Big Wheel-Little Wheel Test of General Motors Corporation. In these tests, Oil D, a base oil containing a premium commercial gear additive package at its recommended dosage level (7 wt %) was used as a control. Another control (Oil E) was another sample of the base oil formulated with a commercial gear additive package (6.5 wt %) treated with a commercially-available limited slip top treat (2 wt %) to provide limited slip properties. The lubricant of this invention was treated with 6.44 wt % of a package containing a product formed as in Example 1 as the limited slip component. The finished lubricant contained 1.91 percent by weight of this limited slip component. The results are summarized in Table 2.

TABLE 2

| Composition | Mileage Accumulated | Results |
| --- | --- | --- |
| Oil D | 4,056 | Stopped due to chatter |
| Oil E | 8,569 | Stopped due to chatter |
| The Invention | 8,000 | No chatter |

Another remarkable feature of the products of this invention is the excellent performance exhibited under the "shock-bump" conditions of the L-42 test, under the rust/corrosion conditions of the L-33 test, and under the high temperature oxidation conditions of the L-37 test when formulated with sulfurized olefin as the sulfur source. Thus a formulated 80W90 gear oil containing by weight 1.338% of a product of this invention made as in Example 1 and 2% of sulfur as sulfurized isobutylene (HiTEC 313 additive; Ethyl Petroleum Additives, Inc.) (Oil F), and another identical gear oil formulation (Oil G) wherein the level of the product of this invention was increased to 2.294%, gave the L-42 test results summarized in Table 3.

TABLE 3

| Test Criteria | Oil F | Oil G |
| --- | --- | --- |
| Pinion Drive/Coast, % Score | 0/8 | 0/11 |
| Ring Drive/Coast, % Score | 0/6 | 0/10 |
| Sequence 3 Ring, Drive/Coast, % Score | 0/0 | 0/0 |

Table 4 summarizes the results of four L-33 tests in which two formulated oils (Oils H and I) contained a commercially-available rust inhibitor (Vaporal) and two formulated oils (Oils J and K) were devoid of conventional rust or corrosion inhibitor. Oils H, I and J contained 1.338 wt % of a product made as in Example 1, whereas Oil K contained 2.294 wt % of that product. The sulfur levels in Oils H and K was 2 wt %, and in oils I and J the sulfur level was 1.2 wt %. The sulfur-containing component in Oil J was di-tert-dodecyl disulfide whereas sulfurized isobutylene (HiTEC 313 additive) was the sulfur-containing component in Oils H, I and K.

TABLE 4

| Composition | Rating Achieved | Rating Needed for Pass |
| --- | --- | --- |
| Oil H | 0 | ≦2.5 |
| Oil I | 2.5 | ≦2.5 |
| Oil J | 1.0 | ≦2.5 |
| Oil K | 0.5 | ≦2.5 |

It will be seen from table 4 that the product of this invention not only possessed antirust properties, but was sufficiently effective in this regard that passing results were achieved with Oils J and K which contained no conventional antirust agent whatsoever.

The high temperature L-37 results summarized in Table 5 again demonstrate the excellent performance of a product of this invention made as in Example 1, especially when formulated with a sulfurized olefin such as sulfurized isobutylene as a sulfur-containing component. The results in Table 5 also illustrate the significance and importance of chain length of the epoxide used in making the product. In particular, Oils M and O contained a product of this invention made as in Example 1 whereas Oils L and N contained a comparative product not of this invention made as in Example 1 except using propylene oxide as the epoxide. On a weight basis Oils L and M had a total phosphorus content of 700 ppm whereas in oils N and O the total phosphorus content was 1200 ppm. Except for the differences in epoxide and in proportions of the product of this invention and the comparative product to reach these total phosphorus levels, the four oils were identical in composition. Each oil contained 3.5 wt % of sulfurized isobutylene (HiTEC 313 additive), and 1.0 wt % of the same phosphorus- and boron-containing dispersant. Therefore the tests focused upon the relative effectiveness of the respective products, namely the product of this invention and the comparative product made the same way with the same materials except for the epoxide.

TABLE 5

| | Oil L | Oil M | Oil N | Oil O |
| --- | --- | --- | --- | --- |
| Phosphorus, ppm | 700 | 700 | 1200 | 1200 |
| Wear | High | Low | Medium | Trace |
| Rippling | Low | Low | Low | Trace |
| Ridging | High | Trace | Medium | Trace |
| Pitting | Low | Low | Low | High |
| Spalling | None | None | None | None |
| Scoring | None | None | None | None |
| Numerical Rating | 216.5 | 6.11 | 111.0 | 10.22 |

The lower the numerical rating in Table 5, the better the result. The product of this invention (Oils M and O) gave passing results. The comparative product (Oils L and N) gave failing results.

The clear superiority of the products of this invention as compared to the above comparative product was also demonstrated in LVFA tests. In these tests comparisons of low velocity friction properties were made among four compositions:

1) A standard commercially-used lubricant specifically formulated for limited slip axle usage where low velocity friction performance is desired (Oil P);

2) An 80W90 base oil devoid of an additive package (Oil Q);

3) The base oil of 2) containing 1000 ppm (wt) of phosphorus as the above comparative product in which propylene oxide was used in its synthesis (Oil R); and 4) The base oil of 2) containing 1000 ppm (wt) of phosphorus as a product made as in Example 1 (Oil S).

The results of these tests are summarized in Table 6 wherein a negative improvement of course means that the test oil composition was less effective than the commercial formulation (Oil P) which was used as the basis for comparison.

TABLE 6

| Composition | % Improvement Over Performance of Oil P |
|---|---|
| Oil Q | −33.45 |
| Oil R | −2.30 |
| Oil S | +6.79 |

In accordance with this invention there are thus provided as additional embodiments thereof, lubricating oil compositions which comprise oil of lubricating viscosity and a phosphorus- and nitrogen-containing composition of the type described hereinabove. The proportions can range from a minor amount of lubricating oil whereby the resultant composition can be an additive concentrate, to a major amount of lubricating oil whereby the resultant composition can be a lubricant composition, such as a gear oil, a transmission fluid, a crankcase lubricant, a hydraulic fluid, a metal-working fluid, etc. The relative proportions can thus be varied within wide limits from as little as 0.05 wt % to as much as 99.95 wt % of the phosphorus- and nitrogen-containing products of this invention.

Another embodiment of this invention is a method of inhibiting limited slip axle or differential noise in a vehicle equipped with a limited slip axle or differential, which comprises lubricating said axle with a lubricating oil composition which comprises a major amount of lubricating oil and a minor of phosphorus- and nitrogen-containing product of this invention. By providing such a lubricant composition for the operation of limited slip axle or differential, the positraction performance of the vehicle is improved. Amounts of the present additive in the finished fullyformulated lubricant for this usage will typically fall in the range sufficient to provide from about 100 to about 5000 ppm (by weight), preferably in the range of 500 to 1500 ppm, and most preferably in the range of 800 to 1200 ppm of phosphorus, and especially about 1000 ppm of phosphorus, in the lubricant.

Still another embodiment of this invention is the provision of additive compositions and lubricating oil compositions which comprise a) an oil-soluble sulfur-containing antiwear/extreme pressure agent in which sulfur is bonded to carbon or to more sulfur, and b) a phosphorus- and nitrogen-containing product of this invention such as described hereinabove.

These compositions are especially useful for operation of equipment or mechanisms in which extreme pressure and antiwear properties are needed, such as vehicular drivelines, gears, heavy duty engines, and the like. As indicated by test results shown above, these additive combinations—especially when the sulfur component is a sulfurized olefin, notably a sulfurized branched chain olefin such as diisobutylene or triisobutylene, and particularly, when the sulfur component is sulfurized isobutylene—provide exceptionally good performance. The relative proportions of these two components may be varied to suit the particular application for which the finished lubricant is intended. Generally speaking however, they will typically be proportioned such that the weight ratio of sulfur as component a) to phosphorus as component b) falls in the range of about 1:1 to about 20:1, and more preferably in the range of about 2:1 to about 10:1. These combined additives are used in lubricating oil compositions. Again, depending on whether the lubricating oil composition is a concentrate for use in making finished lubricants or is itself a finished lubricant composition, the relative proportions between the oil and the combination of components a) and b) can be varied within wide limits from as little as 0.05 wt % to as much as 99.95 wt % of components a) plus b).

This invention is susceptible to considerable variation in its practice. Accordingly, this invention is not intended to be limited by the specific exemplifications set forth hereinabove. Rather, this invention is intended to cover the subject matter within the spirit and scope of the appended claims and the permissible equivalents thereof.

We claim:

1. An oil-soluble phosphorus- and nitrogen-containing composition having limited slip properties formed by (i) reacting (a) an O,O-di-hydrocarbyl phosphorodithioic acid wherein at least 50 mole % of the hydrocarbyl groups are secondary acyclic hydrocarbyl groups free of acetylenic unsaturation and the balance, if any, of the hydrocarbyl groups are primary acyclic hydrocarbyl groups free of acetylenic unsaturation with (b) a monoepoxide or mixture of monoepoxides having in the range of 20 to about 30 carbon atoms in the molecule to form a product, (ii) reacting such product with phosphorus pentoxide to produce an acid phosphate intermediate, and (iii) neutralizing at least a major proportion of the intermediate with at least one amine.

2. A composition in accordance with claim 1 wherein essentially all of the hydrocarbyl groups of said O,O-di-hydrocarbyl phosphorodithioic acid are secondary acyclic hydrocarbyl groups free of acetylenic unsaturation.

3. A composition in accordance with claim 2 wherein said secondary acyclic hydrocarbyl groups are branched chain alkyl groups.

4. A composition in accordance with claim 2 wherein said secondary acyclic hydrocarbyl groups contain from about 6 to about 12 carbon atoms each.

5. A composition in accordance with claim 4 wherein said secondary acyclic hydrocarbyl groups are branched chain alkyl groups.

6. A composition in accordance with claim 1 wherein said O,O-di-hydrocarbyl phosphorodithioic acid consists essentially of 4-methyl-2-pentyl phosphorodithioic acid and said monoepoxide is a mixture of monoepoxides having in the range of 20 to 24 carbon atoms.

7. A composition in accordance with claim 1 wherein said O,O-di-hydrocarbyl phosphorodithioic acid consists essentially of 4-methyl-2-pentyl phosphorodithioic acid and said monoepoxide is a mixture of monoepoxides having in the range of 24 to 28 carbon atoms.

8. A composition in accordance with claim 1 wherein said O,O-di-hydrocarbyl phosphorodithioic acid consists essentially of a mixed di-secondary alkyl phosphorodithioic acid formed from an essentially equimolar mixture of 4-methyl-2-pentanol and 2-propanol, and said monoepoxide is a mixture of monoepoxides having in the range of 24 to 28 carbon atoms.

9. An oil-soluble phosphorus- and nitrogen-containing composition of the formula:

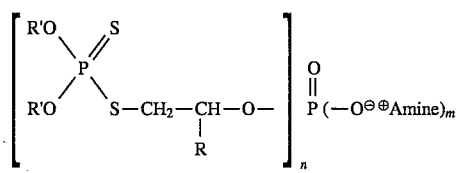

wherein R is one or more alkyl groups having from 18 to about 28 carbon atoms, each R' is, independently, a secondary acyclic hydrocarbyl group free of acetylene unsaturation and having 3 to 18 carbon atoms, Amine is, independently, a protonated primary or secondary amine, n is 1–2, m is 1–2, and the sum of n and m is no greater than 3.

10. A composition in accordance with claim 9 further comprising a minor proportion of an isomeric form of said additive, said isomeric form having the formula:

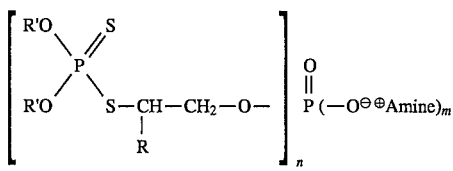

wherein R is one or more alkyl groups having from 18 to about 28 carbons atoms, each R' is, independently, a secondary acyclic hydrocarbyl group free of acetylenic unsaturation and having 3 to 18 carbon atoms, Amine is, independently, a protonated primary or secondary amine, n is 1–2, m is 1–2, and the sum of n and m is no greater than 3.

11. A composition in accordance with claim 9 wherein each R' is a secondary acyclic hydrocarbyl group free of acetylenic unsaturation and having about 6 to about 12 carbon atoms.

12. A composition in accordance with claim 9 wherein each R' is a branched chain secondary alkyl group.

13. A composition in accordance with claim 9 wherein each R' is a 4-methyl-2-pentyl group, and R is a mixture of alkyl groups containing in the range of 18 to 22 carbon atoms.

14. A composition in accordance with claim 10 wherein each R' is a 4-methyl-2-pentyl group, and R is a mixture of alkyl groups containing in the range of 18 to 22 carbon atoms.

15. A composition in accordance with claim 9 wherein R' is a mixture of 4-methyl-2-pentyl groups and 2-propyl groups, and R is a mixture of alkyl groups containing in the range of 22 to 26 carbon atoms.

16. A composition in accordance with claim 10 wherein R' is a mixture of 4-methyl-2-pentyl groups and 2-propyl groups, and R is a mixture of alkyl groups containing in the range of 22 to 26 carbon atoms.

17. A composition in accordance with claim 9 wherein Amine is protonated primary alkyl amine, or protonated primary alkenyl amine having 1 to 3 ethylenic double bonds.

18. A composition in accordance with claim 9 wherein Amine is protonated tertiary alkyl primary amine.

19. A composition in accordance with claim 9 wherein Amine is protonated tertiary alkyl primary amine having about 12 to about 15 carbon atoms per molecule.

20. A composition in accordance with claim 9 wherein Amine is protonated aliphatic primary amine having in the range of about 6 to about 24 carbon atoms.

21. A composition in accordance with claim 9 wherein Amine is protonated aliphatic primary amine having in the range of about 14 to about 20 carbon atoms.

22. A composition in accordance with claim 9 wherein Amine is protonated oleyl amine.

23. A lubricating oil composition which comprises oil of lubricating viscosity and an oil-soluble phosphorus- and nitrogen-containing composition of claim 1.

24. A lubricating oil composition which comprises oil of lubricating viscosity and an oil-soluble phosphorus- and nitrogen-containing composition of claim 2.

25. A lubricating oil composition which comprises oil of lubricating viscosity and an oil-soluble phosphorus- and nitrogen-containing composition of claim 3.

26. A lubricating oil composition which comprises oil of lubricating viscosity and an oil-soluble phosphorus- and nitrogen-containing composition of claim 7.

27. A composition which comprises (a) an oil-soluble sulfur-containing antiwear/extreme pressure agent wherein sulfur is bonded to carbon or to more sulfur, and (b) a phosphorus- and nitrogen-containing composition of claim 1 proportioned such that the weight ratio of sulfur as component a) to phosphorus as component b) falls in the range of about 1:1 to about 20:1.

28. A composition which comprises (a) an oil-soluble sulfur-containing antiwear/extreme pressure agent wherein sulfur is bonded to carbon or to more sulfur, and (b) a phosphorus- and nitrogen-containing composition of claim 2 proportioned such that the weight ratio of sulfur as component a) to phosphorus as component b) falls in the range of about 1:1 to about 20:1.

29. A composition which comprises (a) an oil-soluble sulfur-containing antiwear/extreme pressure agent wherein sulfur is bonded to carbon or to more sulfur, and (b) a phosphorus- and nitrogen-containing composition of claim 3 proportioned such that the weight ratio of sulfur as component a) to phosphorus as component b) falls in the range of about 1:1 to about 20:1.

30. A composition which comprises (a) an oil-soluble sulfur-containing antiwear/extreme pressure agent wherein sulfur is bonded to carbon or to more sulfur, and (b) a phosphorus- and nitrogen-containing composition of claim 7 proportioned such that the weight ratio of sulfur as component a) to phosphorus as component b) falls in the range of about 1:1 to about 20:1.

31. A composition in accordance with claim 27 wherein said sulfur-containing antiwear/extreme pressure agent is sulfurized isobutylene.

32. A composition in accordance with claim 28 wherein said sulfur-containing antiwear/extreme pressure agent is sulfurized isobutylene.

33. A composition in accordance with claim 29 wherein said sulfur-containing antiwear/extreme pressure agent is sulfurized isobutylene.

34. A composition in accordance with claim 30 wherein said sulfur-containing antiwear/extreme pressure agent is sulfurized isobutylene.

35. A method of inhibiting limited slip axle or differential noise in a vehicle equipped with a limited slip axle or differential, which comprises lubricating said axle or differential with a lubricating oil composition which comprises a major amount of lubricating oil and a minor of phosphorus- and nitrogen-containing composition of claim 1.

* * * * *